(12) United States Patent  
Greiner et al.

(10) Patent No.: US 10,179,772 B2  
(45) Date of Patent: Jan. 15, 2019

(54) PROCESS FOR THE ETHERIFICATION OF BIS-RESORCINYOL TRIAZINES

(71) Applicant: DSM IP ASSETS B.V., Heerlen (NL)

(72) Inventors: Nadine Greiner, Kaiseraugst (CH); Sandro Schmid, Kaiseraugst (CH); René Tobias Stemmler, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/571,104

(22) PCT Filed: May 12, 2016

(86) PCT No.: PCT/EP2016/060622  
§ 371 (c)(1),  
(2) Date: Nov. 1, 2017

(87) PCT Pub. No.: WO2016/184766  
PCT Pub. Date: Nov. 24, 2016

(65) Prior Publication Data  
US 2018/0170885 A1    Jun. 21, 2018

(30) Foreign Application Priority Data  
May 18, 2015 (EP) .................................... 15167975

(51) Int. Cl.  
*C07D 251/24* (2006.01)

(52) U.S. Cl.  
CPC .................. *C07D 251/24* (2013.01)

(58) Field of Classification Search  
CPC .................................................. C07D 251/24  
USPC ...................................................... 544/180  
See application file for complete search history.

(56) References Cited

U.S. PATENT DOCUMENTS 5,955,060 A    9/1999 Hueglin et al.

FOREIGN PATENT DOCUMENTS

| GB | 1061521 | 3/1967 |
|----|---------|--------|
| KR | 10-2010-0136227 | 12/2010 |
| WO | WO 94/18278 | 8/1994 |
| WO | WO 2004/106311 | 12/2004 |
| WO | WO 2006/131466 | 12/2006 |
| WO | WO 2010/081835 | 7/2010 |

OTHER PUBLICATIONS

International Search Report for PCT/EP2016/060622, dated Jun. 24, 2016, 4 pages.  
Jiang et al., "Improved synthesis of 6-(4-methoxyphenyl)-2,4-dichloro-1,3,5-triazine and 2,4-bis resorcinyl-substituted UV light absorbing derivatives", Journal of Chemical Research, vol. 11, Jan. 1, 2008, pp. 664-665.

*Primary Examiner* — Kahsay Habte  
(74) *Attorney, Agent, or Firm* — Nixon & Vanderhye P.C.

(57) ABSTRACT

The invention relates to an improved process for the manufacture of bis-resorcinyl triazines of formula (I), wherein $R^1$ is hydrogen, a $C_1$-$C_{18}$ alkyl group or a $C_2$-$C_{18}$ alkenyl group and $R^2$ is a $C_1$-$C_{18}$ alkyl group or a $C_2$-$C_{18}$ alkenyl group. (I)

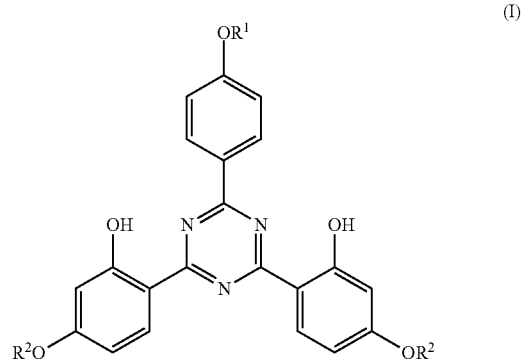

27 Claims, No Drawings

PROCESS FOR THE ETHERIFICATION OF BIS-RESORCINYOL TRIAZINES

This application is the U.S. national phase of International Application No. PCT/EP2016/060622 filed 12 May 2016, which designated the U.S. and claims priority to EP Patent Application No. 15167975.0 filed 18 May 2015, the entire contents of each of which are hereby incorporated by reference.

The invention relates to an improved process for the manufacture of bis-resorcinyl triazines of formula (I), wherein $R^1$ is hydrogen, a $C_1$-$C_{18}$alkyl group or a $C_2$-$C_{18}$alkenyl group and $R^2$ is a $C_1$-$C_{18}$alkyl group or a $C_2$-$C_{18}$alkenyl group.

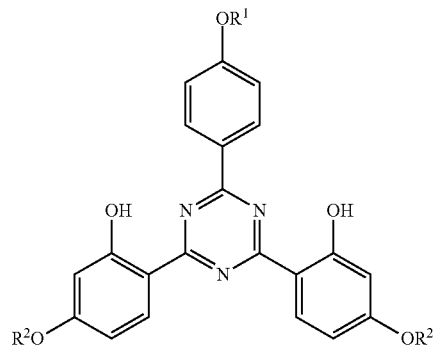

(I)

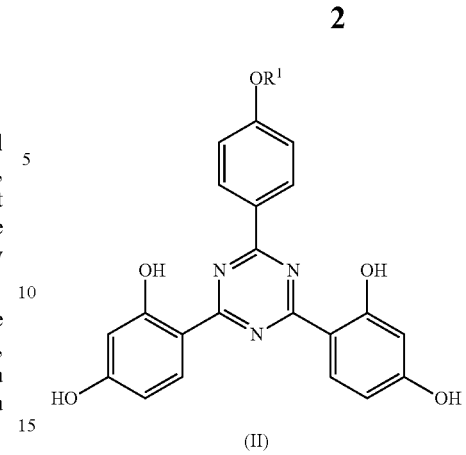

(II)

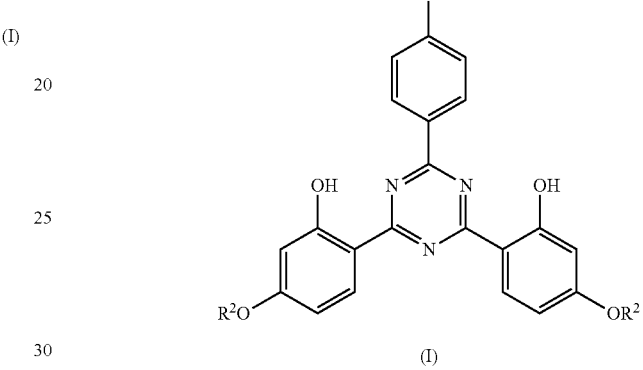

(I)

Bis-resorcinyl triazines of formula (I) such as for example Tinosorb S [INCI Name: Bis-Ethylhexyloxyphenol Methoxyphenyl Triazine] are highly effective UV-absorbers which may, for example, be used as light screening agents in cosmetic products.

The preparation of bis-resorcinyl triazines of formula (I) is known and e.g. disclosed in U.S. Pat. No. 5,955,060. The preparation encompasses the reaction of cyanuric chloride with a phenyl magnesium bromide compound in a Grignard reaction to a dichlorotriazine. The two resorcinyl groups are then introduced by a Friedel-Crafts acylation with resorcinol in the presence of a Lewis acid, in particular an aluminium halide. In a third step, the etherification of the free 4-hydroxyl groups of the resorcinyl residues is carried out by alkylation in the presence of a base. The disclosed alkylation processes of the examples, however, are not satisfactory in view of reaction times, selectivity and yields. Furthermore, the processes involve chromatography techniques to isolate the products, which are tedious, labor intensive and time consuming and thus not suitable for industrial scale as this result in unacceptable manufacturing cost.

Thus, there is a need in the art to develop a simple, industrially feasible and scalable process for the synthesis of bis-resorcinyl triazines of formula (I) that would avoid the aforementioned difficulties.

The present inventors have found an improved process for the preparation of bis-resorcinyl triazines of formula (I) involving specific bases and reaction conditions, which is useful for scale up and results in high yields and purities.

Thus in a first aspect the present invention relates to a process (A) for the preparation of bis-resorcinyl triazines of formula (I), wherein $R^1$ is hydrogen, a $C_1$-$C_{18}$alkyl group or a $C_2$-$C_{18}$ alkenyl group, and $R^2$ is a $C_1$-$C_{18}$alkyl group or $C_2$-$C_{18}$ alkenyl group, said process comprising the step of reacting a bis-resorcinyl triazine of formula (II) in dimethylformamide with an alkyl halide $R^2$—X, wherein X is Cl, Br or I, in the presence of a base, characterized in that the base is selected from the group consisting of sodium carbonate, sodium phosphate and sodium hydrogencarbonate and the reaction temperature is selected in the range of at least 120° C. (at atmospheric pressure).

It is well understood that the reaction temperature would have to be adjusted accordingly if pressure/vacuum would be applied to the process of the present invention, which temperature, however, could easily be adjusted by a person skilled in the art and which embodiment is incorporated herein as well.

Dimethylformamide [CAS 68-12-2] is also known as N,N-Dimethylformamide.

Examples of $C_1$-$C_{18}$alkyl groups or $C_2$-$C_{18}$alkenyl groups are branched or unbranched alkyl, respectively alkenyl groups such as methyl, ethyl, n-propyl, 1-methylethyl, n-butyl, 1-methylpropyl-, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 2-ethylhexyl, n-octyl, n-nonyl, n-decyl, n-undecyl, n-dodecyl, prenyl, 2-propenyl and 3-butenyl groups.

In all embodiments of the present invention $R^1$ is preferably a $C_1$-$C_5$alkyl group, more preferably a $C_1$-$C_2$alkyl group, most preferably a methyl group.

In all embodiments of the present invention $R^2$ is preferably a $C_3$-$C_{10}$alkyl group, more preferably a $C_6$-$C_{10}$alkyl group and most preferably an ethylhexyl group.

In all embodiments of the present invention most preferably $R^1$ is a methyl group and $R^2$ is an ethylhexyl group.

Suitable alkyl halides encompass in particular the respective bromides or chlorides, the chlorides being preferred. Most preferably ethylhexyl chloride [CAS 123-04-6] is used in the processes according to the present invention.

Thus in a particular advantageous embodiment, the invention encompasses a process (B), which is a process (A), wherein $R^1$ is a methyl group, $R^2$ is an ethylhexyl group and the alkyl halide $R^2$—X is ethylhexyl chloride.

Sodium carbonate [CAS 497-19-8], sodium phosphate [CAS 7601-54-9] and sodium hydrogen carbonate [144-55-8] are well known to a person skilled in the art and can e.g. be purchased at Sigma-Aldrich. In all embodiments of the present invention, preferably anhydrous sodium carbonate or anhydrous sodium hydrogen carbonate, most preferably anhydrous sodium carbonate is used. Most preferably anhydrous sodium carbonate with a purity ≥99%, such as preferably with a purity of ≥99.5%, most preferably with a purity of ≥99.9% (assay, calculated based on dry substance) is used in the processes according to the present invention.

Thus, in another advantageous embodiment, the invention encompasses a process (C), which is a process (B), wherein the base is anhydrous sodium carbonate, preferably anhydrous sodium carbonate with a purity of ≥99%, such as preferably with a purity of ≥99.5%, most preferably with a purity of ≥99.9% (assay, calculated based on dry substance).

In all embodiments of the present invention, the reaction temperature (at atmospheric pressure, i.e. 1013 mbar) is preferably selected in the range of 120-155° C., more preferable in the range of 130-155° C., and most preferably in the range of 130-145° C. In a very advantageous embodiment the reaction temperature is selected such that the reaction is maintained at reflux (i.e. a reaction temperature of about 133-143° C., at atmospheric pressure), which can easily be adjusted by a person skilled in the art. If desired the reaction could also be performed under reduced or increased pressure, while the temperature is adjusted accordingly, which is well known by a person skilled in the art. Preferably the reaction is, however, in all embodiments of the present invention carried out at atmospheric pressure.

Thus, in a further advantageous embodiment, the invention encompasses a process (D), which is a process (C), wherein the temperature is selected such that the reaction is maintained at reflux (i.e. at about 133-143° C., at atmospheric pressure).

The reaction time in all processes according to the present invention is generally adjusted such that all of the compound of formula (II) is consumed and the amount of monoalkylated product (i.e. one of $R^2$ is still hydrogen) is <8%, preferably <5%, more preferably <4% (traced by HPLC: area %, detection at 230 nm). Advantageously, the reaction time is selected in the range of 3 to 24 h, preferably in the range of 4 to 20 h, most preferably in the range of 5-15 h.

The molar ratio of the base to the compound of formula (II) is preferably selected in the range of 2 to 9, most preferably in the range of 3 to 7.

Thus, in an additional advantageous embodiment, the invention encompasses a process (E), which is a process (D), wherein the molar ratio of the base to the compound of formula (II) is selected in the range of 3 to 7.

In all embodiments of the present invention, the amount of dimethylformamide is preferably selected such that the amount of the compound of formula (II) in dimethylformamide is in the range of 0.5 to 2 mol/l, preferably in the range of 0.75 to 1.5 mol/l, most preferably in the range of 0.8 to 1 mol/l.

In all embodiments of the present invention, the alkyl halide $R^2$—X is preferably used in a slight excess. Preferably, the amount of the alkyl halide $R^2$—X is selected in the range of 1.5 to 6 mol-equivalents, preferably in the range of 2 to 5 mol-equivalents, more preferably in the range of 2.5 to 4 mol-equivalents, most preferably in the range of 3 to 3.5 mol-equivalents relative to the compound of formula (II).

Thus, in an additional advantageous embodiment, the invention encompasses a process (F), which is a process (E), wherein the amount of dimethylformamide is selected such that the amount of the compound of formula (II) in dimethylformamide is in the range of 0.8 to 1 mol/l and the amount of ethylhexyl chloride is selected in the range of 3 to 4 mol-equivalents relative to the compound of formula (II).

Preferably, the base is added in two portions, the first portion being used to neutralize the solution of the compound of formula (II) in dimethylformamide to about pH 6.5 to 7.5, preferably to about pH 7. Generally about 15-30 wt.-% based on the total amount of the base is to be used for the neutralization step, the amount being easily adjustable by a person skilled in the art.

Thus, in a particular advantageous embodiment the process according to the present invention encompasses the following consecutive steps, wherein all the definitions and preferences as given above also apply:

(i) suspending the compound of formula (II) in dimethylformamide (ii) heating the resulting suspension to 90-155° C., preferably to 95-145° C., until a solution is formed, (iii) neutralization of the resulting solution to about pH 7 with the first portion of the base, (iv) addition of the second portion of the base, followed by the addition of the alkyl halide $R^2$—X (v) heating of the resulting mixture to reflux.

Advantageously, the reaction time in step (v) is selected in the range of 3 to 24 h, preferably in the range of 4 to 20 h, most preferably in the range of 5-15 h.

In a further advantageous embodiment, the process encompasses the further steps of (vi) filtration of the resulting reaction mixture obtained in step (v) followed by (vii) addition of 2-butanol and crystallization of the compound of formula (I) from the dimethylformamide/2-butanol mixture.

The amount of 2-butanol can easily be determined by a person skilled in the art and is preferably selected in the range of 0.5 to 5 l/mol of compound of formula (II), such as preferably in the range of 2 to 4 l/mol of compound of formula (II).

Each reaction of the process according to the invention can in principle be carried out in any reactor suitable for the respective reaction type. Without restricting generality, the following are mentioned by way of example: suspension reactor, stirred tank, stirred tank cascade, tubular reactor, shell-type reactor, shell and tube reactor, fixed-bed reactor, fluidized-bed reactor, reactive distillation column.

EXPERIMENTAL PART 2,4-Bis{[4-(2-ethylhexyloxy)-2-hydroxy]phenyl}-6-(4-methoxyphenyl)-1,3,5-triazine

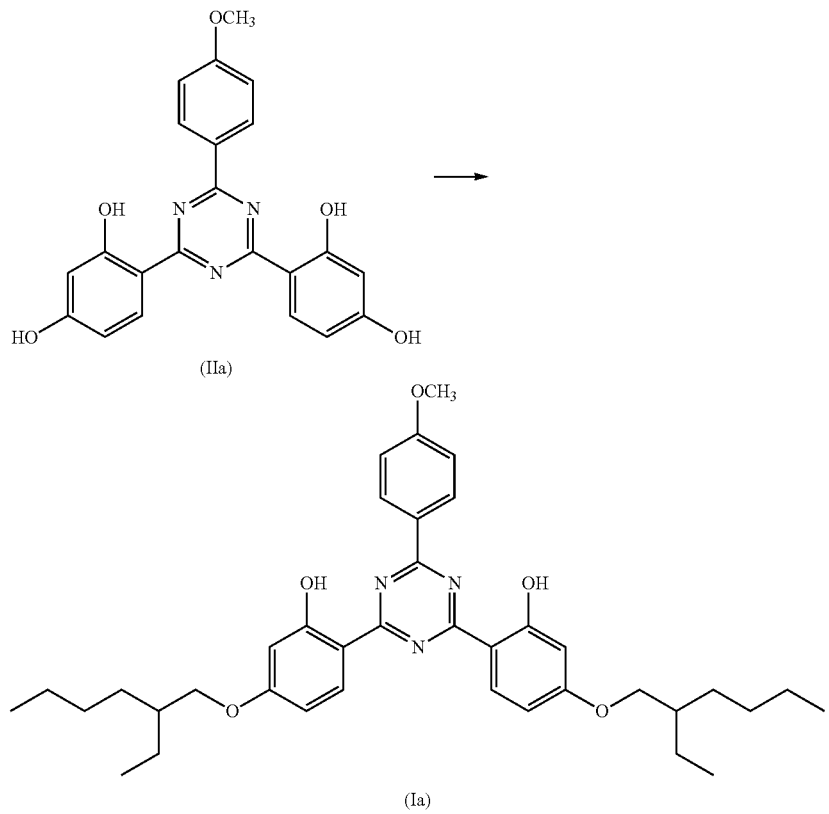

In a 100 ml sulfonation flask equipped with a stirrer, dropping funnel, condenser and internal thermometer, 15 g (31.3 mmol, 84% purity) of 2,4-bis(2,4-dihydroxyphenyl)-6-(4-methoxyphenyl)-1,3,5-triazine (IIa) are introduced together with 35 ml dimethylformamide [and the resulting suspension was heated to 100° C. upon which a clear solution was formed. Then the resulting solution was neutralized with a first portion of the respective base to pH 7. Afterwards, the second portion of the base in the amount as indicated in table 1 was added, followed by the addition of ethylhexyl chloride (EH-Cl, mol-equivalent relative to (IIa)). Then the reaction was heated to reflux (about 133-143° C.), except where indicated otherwise in table 1, until the starting material (IIa) was fully consumed and the amount of the respective mono-alkylated product was <8% (HPLC, detection at 230 nm, relative area % to (Ia) in the reaction mixture). The reaction was then cooled to 80° C. and filtered. The obtained solution was diluted with 90 ml of 2-butanol, cooled to 20° C. and seeded with 2-3 crystals of 2,4-Bis{[4-(2-ethylhexyloxy)-2-hydroxy]phenyl}-6-(4-methoxyphenyl)-1,3,5-triazine (Ia). After complete crystallization (about 3.5 h) the crystals were isolated by filtration resulting in 2,4-Bis{[4-(2-ethylhexyloxy)-2-hydroxy]phenyl}-6-(4-methoxyphenyl)-1,3,5-triazine in the yields and with the purity as illustrated in table 1.

TABLE 1

| Example | Base (mol-eq. relative to (IIa)) | EH-Cl (mol-eq. relative to (IIa)) | t [hours] | Yield[1] [%] | Purity[2] [%] |
|---|---|---|---|---|---|
| 1 Ref | K$_2$CO$_3$ (3.2) | 3.2 | 4.5 h (T = 130° C.) | 62 | 95.4 |
| 2 Ref | K$_2$CO$_3$ (3.2) | 3.2 | 5 h (T = 130° C.) | 59 | 96.7 |
| 3 Ref | Na$_2$CO$_3$ (2.8) | 2.8 | 48 h (T = 105° C.) | 53 | 97.5 |
| 4 Ref | K$_2$CO$_3$ (2.8) | 2.8 | 48 h (T = 105° C.) | 61 | 96.2 |
| 5 Ref | NaOH 50% aq. (2.4) | 2.4 | 95 h (T = 105° C.) | 31[3] | n.a. |
| 6 Ref | K$_2$CO$_3$ (3.5) | 3.5 | 3.5 h | 36 | 96.5 |
| 1 | Na$_2$CO$_3$ (3.5) | 3.5 | 7 h | 85 | 96.6 |
| 2 | Na$_2$CO$_3$ (3.5) | 3.5 | 7 h | 87 | 96.8 |
| 3 | NaHCO$_3$ (3.5) | 3.5 | 8 h | 75 | 96.0 |
| 4 | NaHCO$_3$ (3.5) | 3.5 | 11 h | 78 | 97.1 |
| 5 | Na$_3$PO$_4$ (3.5) | 3.5 | 10.5 h | 65 | 96.3 |

[1] corrected for purity
[2] based on quantitative HPLC
[3] yield based on HPLC area % after 95 h Furthermore, the procedure described in example 1c of U.S. Pat. No. 5,955,060 was followed, resulting, however, in no detectable di-alkylated product even after 90 h. Only mono-alkylated product was detected.

The invention claimed is:
1. A process for preparing bis-resorcinyl triazines of formula (I):

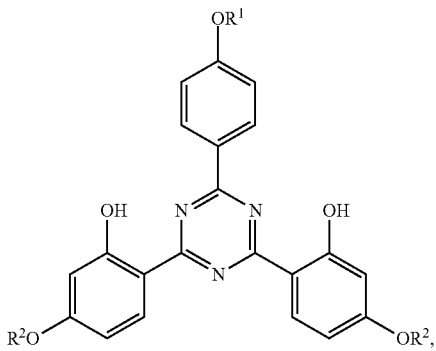

where
R$^1$ is hydrogen, a C$_1$-C$_{18}$alkyl group or a C$_2$-C$_{18}$ alkenyl group, and
R$^2$ is a C$_1$-C$_{18}$alkyl group or C$_2$-C$_{18}$ alkenyl group, wherein
the process comprises the step of reacting a bis-resorcinyl triazine of formula (II):

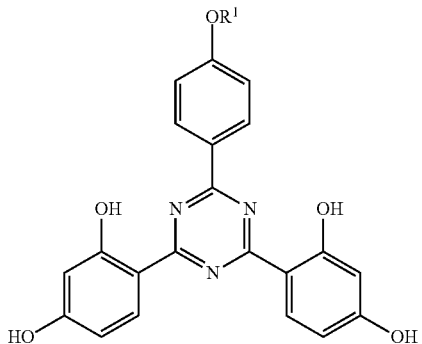

in dimethylformamide with an alkyl halide R$^2$—X, where X is Cl, Br or I, in the presence of a base at atmospheric pressure and at a reaction temperature of at least 120° C. wherein the base is selected from the group consisting of sodium carbonate, sodium phosphate and sodium hydrogencarbonate.

2. The process according to claim 1, wherein R$^1$ is a C$_1$-C$_5$ alkyl group.

3. The process according to claim 1, wherein R$^2$ is a C$_3$-C$_{10}$ alkyl group.

4. The process according to claim 1, wherein R$^1$ is a methyl group and R$^2$ is an ethylhexyl group.

5. The process according to claim 1, wherein the alkyl halide R$^2$—X is an alkyl chloride with X being Cl.

6. The process according to claim 1, wherein the alkyl halide R$^2$—X is ethylhexyl chloride.

7. The process according to claim 1, wherein the base is anhydrous sodium carbonate.

8. The process according to claim 1, wherein the reaction temperature is in a range of 120-155° C.

9. The process according to claim 1, wherein the reaction temperature is such that the reaction is maintained at reflux.

10. The process according to claim 1, wherein the base and the compound of formula (II) are present in a molar ratio of the base to the compound of formula (II) is in a range of 2 to 9.

11. The process according to claim 1, wherein the dimethylformamide is present in an amount such that the amount of the compound of formula (II) in the dimethylformamide is in a range of 0.5 to 2 mol/l.

12. The process according to claim 1, wherein the alkyl halide R$^2$—X is present in an amount in a range of 1.5 to 6 mol-equivalents, relative to the compound of formula (II).

13. The process according to claim 1, wherein the process comprises the following consecutive steps of
(i) suspending the compound of formula (II) in dimethylformamide,
(ii) heating the resulting suspension at atmospheric pressure to a temperature of 90-155° C. until a solution is formed,
(iii) neutralizing the resulting solution of step (ii) to pH 7 by adding a first portion of the base to the solution,
(iv) adding a second portion of the base to the solution, followed by adding the addition of the alkyl halide R$^2$—X to the solution to obtain a mixture, and
(v) heating the resulting mixture of step (iv) to reflux to obtain a reaction mixture.

14. The process according to claim 13, wherein step (v) is practiced for a reaction time of 3 to 24 h.

15. The process according to claim 13, wherein the process further comprises the steps of:
(vi) filtering the resulting reaction mixture obtained in step (v), followed by
(vii) adding 2-butanol to the reaction mixture and crystallizing the compound of formula (I) from the dimethylformamide/2-butanol reaction mixture.

16. The process according to claim 13, wherein step (ii) comprises heating the solution to a temperature of 95-145° C.

17. The process according to claim 14, wherein the reaction time is 4 to 20 h.

18. The process of claim 17, wherein the reaction time is 5-15 h.

19. The process according to claim 2, wherein R$^1$ is a C$_1$-C$_2$ alkyl group.

20. The process according to claim 19, wherein R$^1$ is a methyl group.

21. The process according to claim 3, wherein R$^2$ is a C$_6$-C$_{10}$ alkyl group.

22. The process according to claim 21, wherein R$^2$ is an ethylhexyl group.

23. The process according to claim 10, wherein the molar ratio of the base to the compound of formula (II) is in the range of 3 to 7.

24. The process according to claim 11, wherein the amount of the compound of formula (II) in the dimethylformamide is in the range of 0.75 to 1.5 mol/l.

25. The process according to claim 24, wherein the amount of the compound of formula (II) in the dimethylformamide is in the range of 0.8 to 1 mol/l.

26. The process according to claim 12, wherein the alkyl halide R$^2$—X is present in an amount in the range of 2 to 5 mol equivalents, relative to the compound of formula (II).

27. The process according to claim 26, wherein the alkyl halide R$^2$—X is present in an amount in the range of 2.5 to 4 mol equivalents, relative to the compound of formula (II).

* * * * *